United States Patent [19]

Behan et al.

[11] Patent Number: 5,288,423
[45] Date of Patent: Feb. 22, 1994

[54] PROCESS FOR PREPARING PERFUMED DETERGENT PRODUCTS

[75] Inventors: John M. Behan, Ashford; Jeremy N. Ness, Chartham; Keith D. Perring, Ashford; William M. Smith, Folkstone, all of Great Britain

[73] Assignee: Unilever Patent Holdings, B.V., Rotterdam, Netherlands

[21] Appl. No.: 727,635

[22] Filed: Jul. 10, 1991

[30] Foreign Application Priority Data

Jul. 11, 1990 [EP] European Pat. Off. ........ 90307587.7

[51] Int. Cl.$^5$ ........................... C11D 1/72; C11D 1/74
[52] U.S. Cl. .................... 252/174.11; 252/8.6; 252/8.9; 252/32; 252/315.4; 252/DIG. 5; 252/DIG. 13; 252/DIG. 14
[58] Field of Search .............. 252/174.11, 559, 8.6, 252/8.9, 32, 315.4, DIG. 5, DIG. 13, DIG. 14

[56] References Cited

U.S. PATENT DOCUMENTS

| | | | |
|---|---|---|---|
| 3,944,506 | 3/1976 | Hramchenko et al. | 252/135 |
| 4,202,800 | 5/1980 | Ciko et al. | 252/543 |
| 4,209,417 | 6/1980 | Whyte | 252/174.11 |
| 4,954,285 | 9/1990 | Wierenga et al. | 252/174.11 |
| 5,082,584 | 1/1992 | Loth et al. | 252/174.16 |
| 5,094,761 | 3/1992 | Trinh et al. | 252/8.75 |
| 5,102,564 | 4/1992 | Gardlik et al. | 252/8.75 |
| 5,156,766 | 10/1992 | Behan et al. | 252/312 |

FOREIGN PATENT DOCUMENTS

| | | |
|---|---|---|
| 0217105 | 4/1987 | European Pat. Off. |
| 0316726 | 5/1989 | European Pat. Off. |
| 1439244 | 6/1976 | United Kingdom |

OTHER PUBLICATIONS

Lochhead et al., "Novel Cosmetic Emulsions", Cosmetics & Toiletries, vol. 101, Nov. 1986, pp. 125-138.

Primary Examiner—Anthony McFarlane
Attorney, Agent, or Firm—Cushman, Darby & Cushman

[57] ABSTRACT

The invention concerns a process for incorporating a perfume into a detergent product, wherein the perfume is first combined with one or more non-ionic emulsifiers and an aqueous phase to form a structured emulsion containing liquid crystal structures, which surround the dispersed perfume, and thereafter this structured emulsion is dispersed into a detergent composition. The invention also concerns the detergent products thus obtained. The structured emulsion comprises 1-30% by weight of non-ionic emulsifiers, 1-50% by weight of a perfume and 20-98% by weight of an aqueous phase. The detergent product comprises at least 4% by weight of surfactant.

16 Claims, 1 Drawing Sheet

PROCESS FOR PREPARING PERFUMED DETERGENT PRODUCTS

FIELD OF THE INVENTION

The present invention concerns a process for incorporating perfumes into detergent compositions, particularly laundry and personal hygiene products. More specifically, the invention concerns the use of structured emulsions as vehicles for the incorporation of perfumes into detergent products resulting in products with enhanced perfume performance.

BACKGROUND OF THE INVENTION

The addition of perfumes to detergent products is well established, particularly for detergent products such as household cleansers, laundry products and personal cleaning and cosmetic products. Normally, the perfume is simply admixed with the rest of the detergent composition to produce a homogeneous product but in some cases this process may be facilitated by the use of a solubiliser, such as an emulsifier or co-solvent, to disperse the perfume more readily into the product. Whilst in general the perfume does not contribute to the functional performance of the product it does serve to improve its aesthetic appeal by imparting a pleasing odour to the product both on storage and in use. Additionally it may impart a pleasing odour to substrates on which the product is used, such as skin, hair, fabric etc.

Where a perfume is added to a product the nature of the product can affect its performance in a number of ways. For example, the components of the product may chemically interact with the perfume; the performance of the perfume may be hindered by interactions with component(s) of the product and this may affect both its perception in the package and in use; the longevity of the perfume may be affected. Various methods are known in the art to address these problems. One approach to optimising perfume performance in products is to empirically tailor the perfume by selecting those ingredients which are known in the art to perform well in particular products. In some cases, this can severely constrain creativity in designing a suitable perfume and may have increased cost implications for the successful perfuming of a product. In another approach, encapsulation technology can be used to stop or hinder adverse interactions between perfume and product components or to allow tailored release i.e. to control the release profile. Well-known examples of such encapsulation or controlled delivery technology include processes and products described in EP 303 461 (Unilever), U.S. Pat. No. 3,516,941 (Minnesota Mining & Manufacturing Corp.), EP 332 175 (Lion Corp.), U.S. Pat. No. 4,842,761 (IFF Inc.), EP 334 666 (Union Camp Corp.), GB 2,141,730 (Colgate-Palmolive Co.), EP 332 259 and EP 332 260 (both Procter and Gamble Inc.). Often these methods result in an appreciable on-cost for the perfuming of products.

It is known that liquid crystalline phases can help to stabilise skin cream emulsions (G. Dahms in "Cosmetics and Toiletries", Vol. 101 no. 11 (1986), pp. 113-115) and are claimed to offer advantages in moisture retention on the skin. In a similar way liquid crystalline phases can be used to form vesicles and in recent years there has been extensive literature describing the preparation and application of such vesicles known as "liposomes". Bioemulsifiers, such as phospholipids (e.g. lecithin), have been the principal materials used in the preparation of such liposomes and are being increasingly exploited in a variety of personal products, which are claimed to offer exceptional benefits as skin treatment aids, e.g. as described in EP 120 722 (Parfums Christian Dior), U.S. Pat. No. 4,508,703 (Parfums Christian Dior), U.S. Pat. No. 3,957,971 (Lever Bros. Co.). Additionally, some non-ionic emulsifiers have also been used to form liposomes with similar benefits being claimed, see U.S. Pat. No. 4,217,344 (L'Oreal), U.S. Pat. No. 4,670,185 (Lion Corp.). In WO 88/06883 (Micro Vesicular Systems) paucilamellar vesicles are suggested for a number of applications in the medical and therapeutic field. A method of preparing multilamellar lipid vesicles using certain non-ionic emulsifiers and a sterol is disclosed in WO 88/06882 (Micro Vesicular Systems). A similar method wherein hydrophilic and amphiphilic components are encapsulated in such vesicles is disclosed in WO 88/06881 (Micro-pak Inc.). In EP 347 306 compositions with high perfume concentration are described which appear to contain separate bubbles of non-ionic emulsifier (based on polyglycerol derivatives) and droplets of perfume, surrounded by a continuous aqueous phase.

GB 1,439,244 describes liquid crystalline compositions prepared by mixing an aqueous phase containing an amphoteric surfactant with an organic liquid. This liquid, which may contain perfumery materials, must itself be capable of forming the required liquid crystalline structure in combination with the aqueous phase. However, the organic liquid does not appear to be surrounded, and thus protected, by the liquid crystal structures. The compositions are described as giving enhanced substantivity of the organic liquid to skin, hair etc, when directly applied thereto. Preferably, the aqueous phase of the compositions is acidified to a pH near the isoelectric point of the amphoteric surfactant to obtain maximum substantivity. Finally, the liquid crystalline compositions described lose their substantivity in combination with most anionic surfactants.

On the other hand, EP 217 105 describes, lamellar-type single phase liquid crystal compositions for application the skin, comprising hydrophilic nonionic surfactants having an HLB of 10 or more, water soluble substances, an oily substance and a relatively small amount (preferably below 30%) of water. These compositions are cited to have the advantage of being easily washed of the skin with water, i.e. being the reverse of substantive.

Finally, EP 316 728 and EP 368 146 describe clear microemulsion cleaning compositions comprising anionic and nonionic surfactants, co-surfactants, perfume and water. These products are intended for removing oily and greasy soils.

However, none of these references suggests that such vesicles or liposomes or similar structures would be useful for incorporating a perfume in a detergent product to protect it against interaction with other components present in the detergent product and to enhance its performance.

SUMMARY OF THE INVENTION

It is an object of the invention to provide a simple and economical means of enhancing the performance of perfumes in detergent products by providing a means of separating the perfume from the remainder of the detergent product. Such means would thus give the potential for improved stability in the detergent composition, better sensory impact and may also provide enhanced delivery of the perfume to target substrates. Thus, it is a further object of the invention to optimise the efficiency of perfume delivery to such substrates as fabric, skin, hair, etc. which promotes benefits referred to in the art as "substantivity" or "retentivity". In a similar way, it is a further object of the invention to provide a means of controlling perfume delivery at various stages of the use cycle of a product.

The invention provides a process for incorporating a perfume into a detergent product, whereby the perfume is first combined with one or more non-ionic emulsifiers and an aqueous phase to form a structured emulsion containing liquid crystal structures, which surround the dispersed perfume, and thereafter this structured emulsion is dispersed into a detergent composition, to produce a detergent product with improved perfume performance. The invention also provides detergent products obtainable by this process.

According to the invention the structured emulsion is produced by forming a non-aqueous phase comprising the perfume, a non-ionic emulsifier or mixture based on non-ionic emulsifiers, and optionally other adjuncts, which is mixed at a temperature at which the non-aqueous phase forms a homogeneous liquid; forming an aqueous phase consisting of water or an aqueous solution of water-soluble or water-dispersible materials; and finally mixing the two phases under shear conditions.

DETAILED DESCRIPTION OF THE INVENTION

Figure 1:
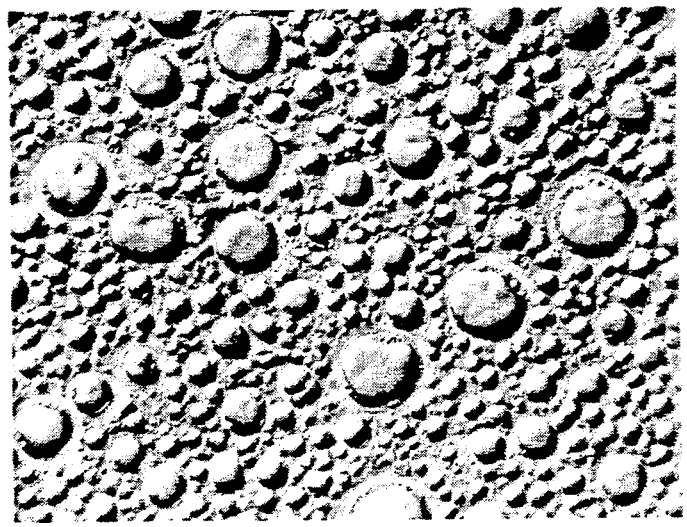
FIG. 1 describes an opaque structure of the emulsion.
Figure 2:
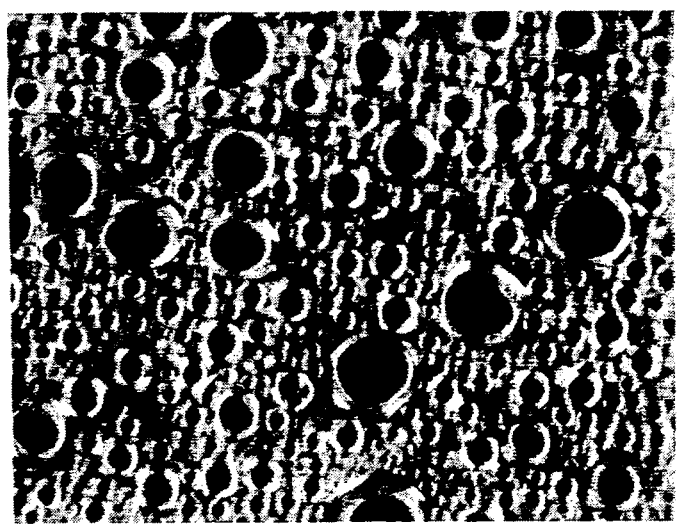
FIG. 2 shows a classical "maltese cross" of the emulsion.

The structured emulsions herein contain 1-50% by weight of perfume in a structured emulsion system comprised basically of one or more non-ionic emulsifiers totalling 1-30% by weight and 20-98% by weight of water or an aqueous mixture containing water-soluble and/or water-dispersible materials, hereinafter jointly referred to as "aqueous phase". Such water-soluble or water-dispersible materials may form up to 30% by weight of the aqueous phase and will hereinafter be referred to as hydrophilic adjuncts. The opaque structured emulsion is characterised by possessing liquid crystalline layers which surround the droplets of perfume. An example of this is depicted in FIG. 1 (see below). The presence of the liquid crystalline system can be illustrated by the use of a polarising light microscope with the sample imaged between crossed polarising filters. FIG. 2 shows the classical "Maltese Cross" contrast typical of such systems (see, for example F. B. Rosevear, J. Am. oil Chemists Soc. (1954), 31 628-639).

Not all non-ionic emulsifiers will by themselves form such structured systems under the conditions of the process described here. In some cases it is advantageous or necessary to promote liquid crystal formation by the addition of structuring aids, such as up to 50% by weight relative to the non-ionic emulsifier(s) of surfactants other than non-ionics (e.g. cetyltrimethylammonium bromide (CTAB) or chloride (CTAC), sodium lauryl sulphate (SLS) sodium dodecylbenzenesulphonate, etc.), and/or up to 100% of sterols (e.g. cholesterol). Preferably the amount of structuring aids is not more than 20% by weight, more preferably 10% or less, relative to the non-ionic emulsifier(s).

Optionally, other hydrophobic adjuncts may be mixed with the perfume and thus be present in the non-aqueous phase at a total level of 0-30% by weight of the non-aqueous phase. For the purpose of this invention it is necessary that the total perfume or perfume/hydrophobic adjunct mixture is hydrophobic in nature as otherwise the emulsion will not form correctly. With the expression "hydrophobic" as used herein is meant a material which will be soluble in one or more organic solvents such as ethanol, acetone or hydrocarbon solvents and will not exhibit an appreciable degree of solubility in water. Examples of such hydrophobic materials other than perfumes include: emollients, oil-soluble polymers, dyes, colourants, humectants, preservatives, anti-oxidants and conditioners.

The non-ionic emulsifiers will preferably be present in the structured emulsion at 4-25% by weight, more preferably 10-20%; the perfume (or perfume/hydrophobic adjuncts mixture) preferably at 10-50% by weight, more preferably 10-40%, particularly 20-40%; and the aqueous phase preferably at 25-86% by weight, more preferably at least 35%, particularly 40-80%. It is particularly suitable that the weight ratio of total emulsifier to perfume lies within the range 1:3 to 3:1 and the weight ratio of non-aqueous phase to aqueous phase lies within the range 1:2 to 4:3, preferably within 1:2 to 1:1. The hydrophobic and hydrophilic adjuncts may together comprise up to 30% by weight of the structured emulsion but preferably comprise no more than 20% by weight.

Non-ionic emulsifiers suitable for use in the present invention as the major liquid crystal-forming emulsifier(s) preferably have a hydrophilic-lipophilic balance (HLB) of less than 10 and are chosen from:

i.a. (Polyethoxylated) fatty alcohols of the formula:

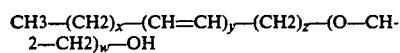

wherein: w ranges from 0-20, preferably from 0-6, more preferably from 0-2 or 2-4; y is 0 or 1; $x+z+2y=11-23$, preferably 11-17.

i.b. Branched (polyethoxylated) fatty alcohols of the formula:

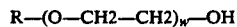

wherein: R is a branched alkyl group of 12-18 carbon atoms and w is as specified above.

ii. Glycerol mono-fatty acid esters, particularly glycerol mono-stearate, oleate, palmitate or laurate.

iii. Fatty acid esters of polyethylene glycol, particularly those of the formula:

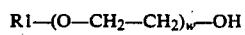

or

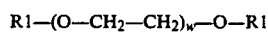

wherein R1 is a stearoyl, lauroyl, oleoyl or palmitoyl residue; w ranges from 2-20, preferably from 2-8.

iv. Sorbitan fatty acid esters, particularly the mono- and tri-esters of the formula:

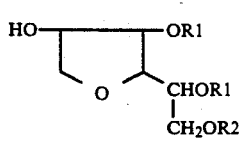

wherein: R1 is H or

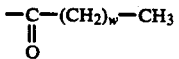

and R2 is

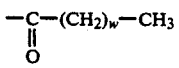

and w ranges from 10–16; preferably w is 16.

v. Polyethoxylated sorbitan fatty acid esters, particularly those of the formula:

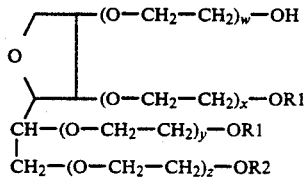

wherein: R1 is H or

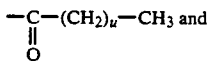

R2 is

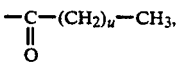

u ranges from 10–16 and the structured emulsion at 4–25% by weight, more preferably 10–20%; the perfume (or perfume/hydrophobic adjuncts mixture) preferably at 10–50% by weight, more preferably 10–40%, particularly 20–40%; and the aqueous phase preferably at 25–86% by weight, more preferably at least 35%, particularly 40–80%. It is particularly suitable that the weight ratio of total emulsifier to perfume lies within the range 1:3 to 3:1 and the weight ratio of non-aqueous phase to aqueous phase lies within the range 1:2 to 4:3, preferably within 1:2 to 1:1. The hydrophobic and hydrophilic adjuncts may together comprise up to 30% by weight of the structured emulsion but preferably comprise no more than 20% by weight.

Non-ionic emulsifiers suitable for use in the present invention as the major liquid crystal-forming emulsifier(s) preferably have a hydrophilic-lipophilic balance (HLB) of less than 10 and are chosen from:

i.e. (Polyethoxylated) fatty alcohols of the formula:

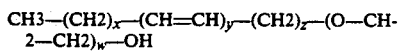

wherein: w ranges from 0–20, preferably from 0–6, more preferably from 0–2 or 2–4; y is 0 or 1; x+z+2y=11–23, preferably 11–17.

i.b. Branched (polyethoxylated) fatty alcohols of the formula:

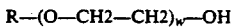

wherein: R is a branched alkyl group of 12–18 carbon atoms and w is as specified above.

ii. Glycerol mono-fatty acid esters, particularly glycerol mono-stearate, oleate, palmitate or laurate. average (w+x+y+z) is 2–20. Preferably, u is 16 and average (w+x+y+z) is 2–4.

In some cases it may be necessary to experimentally select the most suitable emulsifier from those mentioned above, or to use mixtures of these emulsifiers. Also the use of structuring aids as mentioned above will often be helpful in obtaining a liquid crystal structure. The ability of such structuring aids to promote the formation and/or stabilisation of liquid crystals is known in the art. It is important that the non-ionic emulsifiers and structuring aids selected do not interfere with the organoleptic properties of the final product i.e. they should not impart an undesirable odour to the final product.

As used herein the term "perfume" denotes one or a mixture of perfume components, optionally mixed with a suitable solvent, diluent or carrier, which is used to impart a desired odour to the detergent product in the package and/or in use and/or to the substrate that the detergent product is used on.

Perfume components and mixtures thereof which can be used for the preparation of such perfumes may be natural products such as essential oils, absolutes, resinoids, resins, concretes, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Examples of such perfume components are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzylcarbinol, trichloromethylphenycarbinyl acetate, p-tert.butylcyclohexyl acetate, isononyl acetate, vetiveryl acetate, vetiverol, alpha-n-amylcinammic aldehyde, alpha-hexylcinammic aldehyde, 2-methyl-3-(p-tert.butylphenyl)propanal, 2-methyl-3-(p-isopropylphenyl)propanal, 3-(p-tert.butylphenyl)propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyltetrahydropyran, methyl dihydrojasmonate, 2-n-heptylcyclopentanone, 3-methyl-2-pentylcyclopentanone, n-decanal, n-dodecanal, 9-decenol-1, phenoxyethyl isobutyrate, phenylacetaldehyde dimethyl acetal, phenylacetaldehyde diethyl acetal, geranonitrile, citrollonitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellal, ionones, methyl ionones, isomethyl ionones, irones, cis-3-hexenol and esters thereof, indane musk fragrances, tetralin musk fragrances, isochroman musk fragrances, macrocyclic ketones, macrolactone musk fragrances, ethylene brassylate, aromatic nitromusk fragrances.

Suitable solvents, diluents or carriers for perfumes as mentioned above are for example: ethanol, isopropanol, diethylene glycol monoethyl ether, dipropylene glycol, diethyl phthalate, triethyl citrate, etc.

In addition to the components described above, hydrophilic adjuncts may also be present in the structured emulsion at a level of 0-30% by weight of the aqueous phase according to the nature of the detergent product to which the perfume is to be added. Examples of such materials are abrasives, colours, dyes, preservatives, bleaches, optical brighteners, thickeners, emollients, conditioners, water-soluble polymers, water-dispersible polymers, clarifiers, pearlescent agents, salts, therapeutic agents, structurants, stabilisers, water-soluble perfumes, organic solvents.

The structured emulsion described herein can be formed under a variety of conditions, according to the particular emulsifiers chosen and the perfume to be emulsified In general, the method of manufacture consists of separately forming the non-aqueous phase and the aqueous phase and then mixing the two phases under shearing conditions to form the final emulsion and continuing to mix while bringing the mixture to ambient temperature (if necessary). The mixing process is rapid in most cases, but for more viscous products (i.e. high emulsifier levels or viscous perfumes) it may be necessary to mix slowly or over an extended period to produce a homogeneous emulsion. The non-aqueous phase consists of the perfume (or perfume/hydrophobic adjuncts mixture), emulsifier (mixture) and optional structuring aids, and is mixed at a temperature at which it forms a homogeneous liquid, wherein "homogeneous" is defined as the absence of discrete solid particles or droplets of liquid in the non-aqueous phase. The aqueous phase, optionally containing up to 30% by weight of hydrophilic adjuncts, is preferably brought to substantially the same temperature as the non-aqueous phase before mixing the two phases. In this connection "substantially the same temperature" is intended to mean such temperature that after mixing the complete emulsion has a temperature at which the non-aqueous phase would have formed a homogeneous liquid. Low temperature processing may thus be possible for those non-ionic emulsifiers or emulsifier mixtures that are liquid at room temperature. In many cases the order of mixing the two phases is not critical, although normally the non-aqueous phase is added to the aqueous phase. In addition, although the shear rate used for mixing will affect to some extent the ultimate droplet size of the emulsion, the actual shear rate used is not critical in most cases for formation of the emulsion. Use of too high a shear rate with relatively viscous emulsions can result in destabilisation of the emulsion system. The emulsions of the invention are suitably prepared under conditions of low shear, using mixers providing shear rates within the range of $10-1400s^{-1}$ Preferred shear rates lie within the range of $15-500s^{-1}$ which values are considerably lower than those provided by high shear mixers/homogenisers such as Microfluidisers (trademark of Microfluidics Corp.). Suitable information on shear rates and fluid behaviour in mixing vessels can be found in Perry's Chemical Engineer's Handbook, sixth edition, D. Green (editor), McGraw-Hill, 1984. Thus, although both high and low shear rate mixers can be used, low shear rate mixers are generally preferred (even laboratory magnetic stirrers are suitable), so obviating the need for complicated and expensive equipment and improving the economics of the process. For the examples described below, the droplets will have diameters typically lying in the range of 0.2-50 $\mu$m, with the majority of them (on a weight basis) having a droplet size above 1 $\mu$m. The resulting emulsion is opaque.

Addition of the structured emulsion to a detergent composition to form the final detergent product can be accomplished in a number of ways. Although it is preferable to add the emulsion at the final stage of product manufacture, it is possible in some cases to incorporate it at an intermediate stage. The high levels of surfactant present in the detergent products according to the invention might be expected to be sufficient to solubilize the perfume and the structuring emulsifier thus leading to loss of the structure and loss of the benefits in perfume stability and delivery.

However, even where the emulsion system appears to be fully solubilized, or at least the emulsion droplet size is reduced to the point where light microscopy can no longer detect them, surprisingly these benefits are still achieved For example, addition of the emulsion of example 1 to the shampoo of example 19 results in a clear shampoo product with enhanced perfume performance. Without being bound by theory, it is hypothesised that a degree of structuring, whereby the perfume is still intimately associated with the structured emulsion system, still exists in the product, although the scale of the structure would be reduced compared with the initial emulsion system.

In addition, it is preferred to add the emulsion to the detergent composition at or about ambient temperature. Higher temperatures may be used but this is usually not necessary and may result in loss of perfume (or particular perfume components) through evaporation. In general, mixing is continued until the emulsion is evenly dispersed through the product (typically 5-30 minutes—depending on the scale of the operation and the particular emulsion/detergent composition). In the case of solid products, such as laundry powders, it may not be possible to achieve a completely homogeneous product, but this will not adversely affect perfume performance. Mixing is preferably carried out under low shear conditions.

The final detergent products as described herein mainly comprise products used for domestic and personal cleaning purposes. Examples are: laundry products such as laundry washing powders, laundry washing liquids and fabric conditioners; domestic hard surface and general purpose cleaners; dishwashing powders or liquids; bleaching powders and bleaching liquids; personal washing products such as solid or liquid toilet soaps, foam bath products, shower gels, shampoos etc. They are characterized by generally possessing a relatively high level of surfactant i.e. generally between 4 and 90%, typically between 4 and 75% by weight, which may be anionic, cationic, non-ionic or amphoteric or mixtures thereof, whereby the proportion of non-ionics will generally be less than half and usually much less than half the total amount of surfactant in the detergent product. Furthermore, detergent products according to the invention generally comprise 0.15-95% by weight of water, 0.01-30% of perfume and 0-60% of optional adjuncts, such as abrasives, preservatives, colours, dyes, bleaches, optical brighteners, thickeners, emollients, conditioners, clarifiers, pearlescent agents, salts, therapeutic agents, structurants, stabilisers, solvents and co-solvents. The total of these ingredients in a detergent product with the exception of perfume is hereinafter referred to as "detergent composition". Apart from the perfume added to this detergent composition as a structured emulsion according to the invention, the product may also contain a quantity of perfume added in the conventional way.

The exact composition of the detergent products according to the invention naturally depends on the type of product and outlines of such compositions for some products are presented below.

Thus, a shampoo will generally comprise 5-25% by weight of an anionic surfactant, e.g. an alkyl sulphate or an alkyl ether sulphate, or an amphoteric surfactant, e.g. a betaine. It may also contain 0-10% of non-ionic surfactant or other amphoteric or cationic surfactants as foam boosters or viscosity modifying agents; 0-5% of additional adjuncts such as chelating agents, anti-oxidants, dyes, pearlescent agents, preservatives, conditioning agents, sunscreen agents, anti-dandruff actives and salts; 58-95% of water. The perfume content generally is 0.2-2.0% by weight.

Solid or liquid soaps generally comprise at least 15% by weight and preferably at least 25% of one or more surfactants chosen from: salts of C12-C18 fatty acids, C12-C18 fatty acid mono- and di-ethanolamides, salts of lauryl and myristyl sulphate, salts of lauryl and myristyl ether sulphates, and betaines. The remainder comprises water, perfume, and optional foam boosters, electrolytes, anti-oxidants, emollients, moisturisers and fillers.

Foam bath products generally comprise 5-75% by weight of an anionic surfactants, e.g. an alkyl sulphate or alkyl ether sulphate, sulphosuccinate or taurate, or an amphoteric surfactant, e.g. a betaine. It may also contain 5-15% of non-ionic or amphoteric surfactants as foam boosters or viscosity modifiers; 0-5% of additional adjuncts such as chelating agents, skin conditioning agents, emollients, anti-oxidants, preservatives, dyes, pearlescent agents and salts; 3-90% of water. The perfume content generally is 0.2-3% by weight. Shower gels generally comprise 5-30% of an anionic surfactant e.g. an alkyl sulphate or alkyl ether sulphate, or an amphoteric surfactant, e.g. a betaine. It may also contain 0-10% of non-ionic or amphoteric surfactants as foam boosters or viscosity modifiers; 0-10% of additional adjuncts such as chelating agents, skin conditioning agents, emollients, anti-oxidants, preservatives, dyes and salts; 47-95% water. The perfume content is generally 0.2-3% by weight. Laundry washing powders generally comprise 5-30% by weight of anionic surfactants e.g. alkylbenzenesulphonates, fatty acid soaps, alcohol sulphates or alpha-olefin sulphonates; 1-10% of non-ionic surfactants such as polyethoxylated alcohols; 0-5% of lather boosters such as alkanolamides; 35-60% of inorganic builders/fillers such as sodium tripolyphosphate, zeolites, sodium carbonate, sodium sulphate or sodium silicate; 0-15% of bleaching agents such as sodium perborate and bleach precursors such as tetraacetylethylenediamine; up to 15% of additional adjuncts such as optical brightening, chelating agents, anti-redeposition agents, enzymes, dyes, and perfume; 2-15% of water.

Laundry washing liquids generally comprise 5-40% by weight of anionic surfactants, e.g. fatty acid soaps or alkylbenzenesulphonates; 1-20% of non-ionic surfactants, e.g. (poly)ethoxylated alcohols and alkanolamides; 0-30% of builders/sequestrants, e.g. sodium tripolyphosphate, tetrapotassium pyrophosphate, soda ash and silicates; 0-15% of alcohols/coupling agents, e.g. ethanol, glycerol and sodium xylenesulphonate; 1-5% of additional adjuncts such as anti-redeposition agents, optical brighteners, enzymes, fabric conditioning agents, dyes and perfume; 40-60% of water.

Fabric conditioners generally comprise 4-50% by weight of cationic actives e.g. quaternary ammonium or imidazoline derivatives, and additionally 0-5% of other lubricants such as lanolin or fatty acids; 0.5-5% of additional adjuncts such as preservatives, dyes, pH control agents, co-solvents, opacifiers, electrolytes and perfume; 49.5-95.5% of water.

Domestic cleaners generally comprise 3-15% of anionic surfactants, e.g. linear alkylbenzenesulphonates, ethoxylated alcohol sulphate or soap; 0-3% of non-ionic surfactant, e.g. fatty acid alkanolamides; 0-5% of alcohols or polyols, 0-45% of inorganic fillers; 0.5-5% of additional adjuncts such as preservatives, dyes, thickeners, hydrotropes and perfume; 27-96.5% of water. Liquid bleach products generally comprise 5-15% by weight of bleaching agent, e.g. sodium hypochlorite; 2-8% of ampholytic surfactant. e.g. alkyl amine oxides; 0-2% of anionic surfactant, e.g. alpha-olfein sulphonate or soap; 0.1-2% of additional adjuncts such as dyes, electrolytes, thickeners and perfume; 73-93% of water.

The improved perfume performance brought about by the process of the invention is particularly valuable for detergent products which are intended to come into contact with skin, hair or fabric, i.e. for laundry products and personal washing products.

FIG. 1 is a transmitted light micrograph of the structured emulsion of example 10. FIG. 2 is a crossed polars image of the same area as FIG. 1.

EXAMPLES

I. Structured emulsions production

Examples of emulsions produced according to the process described in this patent are given in table 1. They were produced by the following method:

i. A non-aqueous phase P is formed by mixing the following components:
  A: one or more non-ionic emulsifiers;
  B: a perfume according to one of the recipes A, B, C or D;
  C: optionally one or more structuring aids;
  whilst maintaining the temperature of the phase P at a sufficiently high level to obtain a homogeneous liquid.

ii. An aqueous phase Q is formed, consisting of water optionally containing one or more hydrophilic adjuncts and brought at substantially the same temperature as phase P;

iii. The phases P and Q are mixed and brought to room temperature whilst continuing to mix.

Perfumes according to the following recipes were used in the emulsion examples

| | | % |
|---|---|---|
| Perfume A | Coumarin | 0.5 |
| | Benzyl acetate extra | 4.0 |
| | Benzyl salicylate | 10.0 |
| | Dihydromyrcenol | 10.0 |
| | Citronellol | 10.0 |
| | Methyl cedryl ketone | 8.0 |
| | Methyl dihydrojasmonate | 5.0 |
| | 2-Phenylethanol | 10.0 |
| | 5-Acetyl-3-isopropyl-1,1,2,6-tetramethylindane | 7.5 |

-continued

|            |                                                                      | %    |
|------------|----------------------------------------------------------------------|------|
|            | Jasmopyrane forte                                                    | 10.0 |
|            | Linalool                                                             | 10.0 |
|            | Alpha-hexylcinnamic aldehyde                                         | 8.0  |
|            | Isolongifolanone                                                     | 3.0  |
|            | Styrallyl acetate                                                    | 1.0  |
|            | Methylionone                                                         | 3.0  |
| Perfume B  | 1,3,4,6,7,8-hexahydro-4,6,6,7,8,8-hexa-methylcyclopenta(g)-2-benzopyran | 7.5  |
|            | Methyl cedryl ketone                                                 | 12.0 |
|            | Lilial                                                               | 7.0  |
|            | Benzyl salicylate                                                    | 7.2  |
|            | Alpha-hexylcinnamic aldehyde                                         | 13.0 |
|            | Methyl dihydrojasmonate                                              | 14.6 |
|            | 2-Phenylethanol                                                      | 9.0  |
|            | Dipropylene glycol                                                   | 18.0 |
|            | Litsea cubeba oil                                                    | 5.0  |
|            | Coumarin                                                             | 0.1  |

-continued

|           |                         | %    |
|-----------|-------------------------|------|
|           | 2-Hexyl-2-cyclopentenone | 3.3  |
|           | Coumarin                | 2.0  |
|           | Hexyl benzoate          | 6.7  |
|           | Ethyl cinnamate         | 1.5  |
|           | Diethyl phthalate       | 15.0 |
| Perfume D | Cineole                 | 15.0 |
|           | Borneol                 | 10.0 |
|           | Cedar wood oil          | 18.0 |
|           | Clove terpenes          | 2.0  |
|           | Pine oil American       | 10.0 |
|           | Diphenyl oxide          | 1.0  |
|           | Tetrahydrolinalool      | 6.0  |
|           | Fenchyl acetate         | 5.0  |
|           | Benzyl benzoate         | 15.0 |
|           | Isobornyl acetate       | 18.0 |

TABLE 1

Examples of emulsion systems

| Example no. | Phase P A | Phase P B | Phase P C | Phase Q |
|---|---|---|---|---|
| 1 | Brij 52 5.00 g | Perfume A 5.00 g | | Water 20.0 g |
| 2 | Brij 52 4.50 g | Perfume A 5.00 g | CTAB 0.50 g | Water 20.0 g |
| 3 | Arlacel 129 5.00 g | Perfume B 5.00 g | | Water, Dye 20.0 g, 0.05 g |
| 4 | Arlacel 129 10.0 g | Perfume B 50.0 g | Cholesterol 1.50 g | Water 200 g |
| 5 | Span 20 8.00 g | Perfume C 40.0 g | | Water 160 g |
| 6 | Cithrol 2MO 15.0 g | Perfume D 45.0 g | CTAB 1.0 g | Water 300 g |
| 7 | Brij 30 1.00 g | Perfume C 3.00 g | CTAC 0.15 g | Water 10.0 g |
| 8 | Brij 72, 721 12.0 g, 6.0 g | Perfume A 27.0 g | | Water 80.0 g |
| 9 | Brij 58, Cetyl alcohol 8.0 g 12.0 g | Perfume C 20.0 g | | Water 60.0 g |
| 10 | Span 60 20.0 g | Perfume C 15.0 g | CTAB 2.00 g | Water 65.0 g |
| 11 | Brij 52 7.0 g | Perfume A 23.0 g | | Water 50.0 g |
| 12 | Brij 52 7.0 g | Perfume B 23.0 g | | Water 30.0 g |
| 13 | Tweeen 61 15.0 g | Perfume C 17.0 g | SLS 1.50 g | Water, Dye 65.0 g, 0.05 g |
| 14 | Tween 60, 61 4.0 g, 10.0 g | Perfume B 15.0 g | CTAB, Cholesterol 1.00 g 1.00 g | Water, Preserv. 60.0 g, 0.30 g |
| 15 | Brij 52, 58 20.0 g, 5.0 g | Perfume D 36.0 g | | Water 130 g |
| 16 | Brij 30 20.0 g | Perfume A 10.0 g | | Water 70.0 g |
| 17 | Empilan KM20, Laurex CS 2.0 g 4.0 g | Perfume B 10.0 g | | Water 14.0 g |

Key to table 1:
Brij, Arlacel, Span and Tween are trademarks of ICI Speciality Chemicals.
Cithrol is a trademark of Croda Chemicals Ltd.
Empilan and Laurex are trademarks of Albright & Wilson Ltd.
CTAC = Cetyltrimethylammonium chloride.
CTAB = Cetyltrimethylammonium bromide.
SLS = Sodium lauryl sulphate

|           |                                         |      |
|-----------|-----------------------------------------|------|
|           | Linalool                                | 3.6  |
|           | Hexyl salicylate                        | 3.0  |
| Perfume C | Benzyl salicylate                       | 6.5  |
|           | P-tert.butylanisole                     | 5.0  |
|           | Hexyl salicylate                        | 4.5  |
|           | P-tert.butylcyclohexyl acetate          | 12.0 |
|           | O-tert.butylcyclohexyl acetate          | 3.5  |
|           | 4-Acetoxy-3-pentyltetrahydropyran       | 8.5  |
|           | 2-Phenylethanol                         | 7.5  |
|           | Phenylethyl acetate                     | 0.5  |
|           | Alpha-hexylcinnamic aldehyde            | 5.0  |
|           | 2,4-dimethyl-3-cyclohexene-1-carboxaldehyde | 1.5 |
|           | Methyl cedryl ketone                    | 5.0  |
|           | 5-Acetyl-3-isopropyl-1,1,2,6-tetramethylindane | 2.0 |

II. Detergent products

The following products were prepared by the addition of the indicated structured emulsion system, made up as above, to the product base under mild mixing conditions (ambient temperature, low shear).

Example 18. Shampoo

|                  | g    |
|------------------|------|
| Texapon ALS (1)  | 34.0 |
| Texapon NA (1)   | 21.0 |
| Ammonium Chloride | 0.9 |

Example 18. Shampoo

| | g |
|---|---|
| Purified water | 43.6 |
| Preservative | q.s. |
| Structured emulsion example 2 | 3.0 |

(1) Henkel KGaA

The Texapon ALS and Texapon NA were stirred into the water and then the ammonium chloride was dissolved into this mixture together with the preservative. Finally the perfume emulsion was stirred into the shampoo base.

The shampoo was evaluated as follows. 1 g of shampoo was used for each 10 g (dry weight) of hair (switches of Yugoslavian Red Tie Hair [Raoul Ltd., London]). The hair was rinsed in warm tap water and combed to ensure that it was odourless and tangle-free. Shampoo was then massaged into the hair for 30 seconds and the switch was left standing for 1 minute before rinsing for 30 seconds. This procedure was then repeated and finally excess moisture squeezed out by hand. Odour assessment was carried out at this stage and after drying (air dry or hot blow dry).

Table 2 shows the sensory results of a panel assessment of wet and blow-dried hair switches. The rank sum analysis of these results indicate the test shampoo (S1) to be far superior in perfume impact to two controls S2 and S3. S2 is a shampoo composition as S1, but with perfume A in the same concentration added as neat perfume instead of as structured emulsion. S3 is the same shampoo composition as S2, but also including the non-perfume components of the structured emulsion of example 2 added separately.

TABLE 2
Sensory assessments of washed hair switches

| Stage | Shampoo | A | B | C | D | E | F | G | H | I | J | K | S |
|---|---|---|---|---|---|---|---|---|---|---|---|---|---|
| Wet | S1 | 2 | 1 | 1 | 1 | 1 | 1 | 1 | 2 | 1 | 1 | 1 | 13 |
| | S2 | 1 | 2 | 2 | 2 | 3 | 2 | 2 | 1 | 3 | 2 | 2 | 22 |
| | S3 | 3 | 3 | 3 | 3 | 2 | 3 | 3 | 3 | 2 | 3 | 3 | 31 |
| Dry | S1 | 2 | 1 | 1 | 1 | 1 | 1 | 1 | 2 | 1 | | | 11 |
| | S2 | 1 | 2 | 2 | 2 | 2 | 2 | 2 | 1 | 2 | | | 16 |
| | S3 | 3 | 3 | 3 | 3 | 3 | 3 | 3 | 3 | 3 | | | 27 |

Ranking: 1 = Best, 3 = Worst; S = rank sum

Example 19. Shampoo

| | g |
|---|---|
| Empicol ESB3 (1) | 45.0 |
| Tegobetain L7 (2) | 7.00 |
| Empilan CDE (1) | 1.00 |
| Citric acid to pH 6.5 | |
| Sodium Chloride | 0.70 |
| Purified Water | 45.95 |
| Structured emulsion example 1 | 2.10 |

(1) Albright and Wilson Ltd. (2) Th Goldschmidt Ltd.

The Empicol ESB3, Tegobetain L7, Empilan CDE and water were blended with gentle warming until homogeneous. After cooling, the pH was adjusted with the citric acid and the preservative added. Finally the perfume emulsion was stirred into the shampoo base.

The test shampoo was assessed olfactorily using standard triangle testing techniques with a trained panel of 30 persons. The triangle tests showed that panellists could differentiate between samples washed with the test system and those washed with the control system (containing the same perfume A at the same concentration). The panellists were asked "Which hair switch smells strongest of perfume?" 22 out of the 30 panellists chose the switches washed with the test shampoo as having the strongest perfume odour.

Example 20 Laundry Liquid

| | g |
|---|---|
| Nansa SL 30 (1) | 37.70 |
| Texapon N70 LS (2) | 4.60 |
| Empiphos STP (1) | 11.00 |
| Tetrakal (1) | 4.00 |
| Sodium Carbonate | 1.75 |
| Tinopal CBS-X (3) | 0.20 |
| Preservative | q.s. |
| Water | 40.45 |
| Structured emulsion of example 9 | 1.75 |

(1) Albright and Wilson Ltd; (2) Henkel KGaA; (3) Ciba-Geigy AG

The Empiphos STP, Tetrakal, Tinopal CBS-X and sodium carbonate were dissolved in the water with warming. The Texapon and Nansa were then warmed together and stirred gently into the aqueous phase and the resulting mixture stirred until cool and homogeneous. The preservative and perfume emulsion were then gently stirred in to form the final product.

Laundry liquid prepared by the above procedure was stored for two months at ambient temperatures. A control was also made, using neat perfume C (at the same concentration), and treated similarly. Samples of Terry towelling (40 g) were washed in aqueous solutions of these laundry liquids (0.25% w/w) at ambient temperatures using a commercial washing machine simulator (Tergotometer) for twenty minutes. The cloths were then hand wrung and assessed by a team of expert evaluators for fragrance intensity both wet and after air drying for one week. At both stages the cloths washed in the test system were found to have higher perfume intensity than those washed in the control system.

Example 21. Laundry Powder

| | g |
|---|---|
| Phase A: | |
| Sodium Carbonate | 27.00 |
| Sodium Bicarbonate | 10.00 |
| Sodium Aluminosilicate | 30.00 |
| Sodium Silicate | 5.00 |
| Sodium Sulphate | 6.75 |
| Optical Brightener | 1.00 |
| Phase B: | |
| Synperonic A7 (1) | 18.00 |
| Protease (2) | 2.00 |
| Phase C: | |

-continued
Example 21. Laundry Powder

| | g |
|---|---|
| Structured emulsion of example 13 | 1.45 |

(1) ICI Speciality Chemicals (2) Novo Industries Ltd.

Phase A was ground and blended and then slurried with water and spray dried. Phase B was mechanically mixed into the resultant powder and finally phase C was also mechanically mixed in.

Example 22. Liquid fabric conditioner

| | g |
|---|---|
| Arquad 2HT (75%) (1) | 7.50 |
| Purified Water | 92.25 |
| Dye | 0.01 |
| Preservative | q.s. |
| Structured emulsion of example 10 | 1.70 |

(1) Akzo Chemie BV

The Arquad was stirred into the water and after mixing to a homogeneous product, the preservative, dye and structured emulsion were added.

Example 23. Shower Gel

| | g |
|---|---|
| Empicol ESB 3 (1) | 50.00 |
| Empilan CDE (1) | 2.00 |
| Cetiol HE (2) | 5.00 |
| PEG 6000 DS (3) | 3.50 |
| Preservative/Dye | q.s. |
| Purified Water | 39.15 |
| Structured emulsion of example 14 | 2.10 |

(1) Albright and Wilson Ltd; (2) Henkel KGaA; (3) Akzo Chemie BV.

The PEG 6000 DS was heated with the Empicol ESB3 until dissolved. The Empilan CDE and Cetiol HE were then mixed in and the water added. This was then mixed well and allowed to cool. The preservative and dye were then added and finally the structured emulsion gently stirred in. After storage for four weeks the test shower gel was assessed by an expert fragrance evaluator against a control formulation (as above but with the perfume added neat) for perfume impact during an arm wash test. It was found that the test system showed a noticeable increase in perfume substantivity (perfume impact on skin after drying).

Example 24. Liquid Soap

| | g |
|---|---|
| Phase A: | |
| Empicol ESB 3 (1) | 52.60 |
| Empilan CDE (1) | 2.00 |
| Ethylene GMS | 2.00 |
| Tegobetain L7 (2) | 10.00 |
| Preservative | q.s. |
| Witconol CD-18 (3) | 0.20 |
| Phase B: | |
| Crotein O (4) | 1.00 |
| D-Panthenol (5) | 0.50 |
| Deionised water | 33.40 |
| Phase C: | |
| Structured emulsion of example 12 | 0.80 |

(1) Albright and Wilson Ltd.; (2) Th Goldschmidt AG; (3) Witco Chemical Corp.; (4) Croda Chemicals Ltd.; (5) F Hoffmann La Roche.

Phase A was warmed to 65° C. and mixed until all the ingredients had dissolved. One-third of phase B was then added to phase A. This mixture was then cooled to 35° C. and the perfume added. The remainder of phase B was then added at 27° C.

Example 25. Bleach Product

| | g |
|---|---|
| Sodium hypochlorite (15% Chlorine) chlorine) | 88.93 |
| Empigen OB (1) | 10.00 |
| Sodium hydroxide | 1.00 |
| Potassium chromate | 0.02 |
| Structured emulsion of example 15 | 0.10 |

(1) Albright and Wilson Ltd.

The Empigen OB was blended into the hypochlorite solution. The potassium chromate was then added, followed by the sodium hydroxide. Finally the perfume emulsion was gently mixed into the bleach solution (it is advisable to use protective equipment at all stages). The perfume for the control sample was added with the Empigen.

We claim:

1. A process for incorporating a perfume into a detergent product comprising the steps of:
   combining a dispersed perfume with one or more non-ionic emulsifiers at a temperature sufficient to form a homogeneous non-aqueous liquid phase;
   heating an aqueous phase, consisting essentially of water, to a temperature substantially the same as the non-aqueous liquid phase;
   mixing the aqueous phase and non-aqueous phase under shear conditions such that an emulsion containing liquid crystal structures, which surround the dispersed perfume is formed;
   dispersing the structured emulsion into a detergent composition.

2. A process according to claim 1 wherein the emulsion comprises 1–30% by weight of non-ionic emulsifiers, 1–50% by weight of a perfume and 20–98% by weight of an aqueous phase.

3. A process according to claim 2 wherein the non-ionic emulsifiers are chosen from
   i. Fatty alcohols and polyethoxylated fatty alcohols of the formula:

$$CH_3-(CH_2)_x-(CH=CH)_y-(CH_2)_z-(O-CH_2-CH_2)_w-OH$$

wherein: w ranges from $0 \geq 20$; y is 0 or 1; $x + z + 2y = 11-23$;

ii. Branched fatty alcohols and polyethoxylated fatty alcohols of the formula:

$$R-(O-CH_2-CH_2)_w-OH$$

wherein: R is a branched alkyl group of 12–18 carbon atoms and w is as specified above;

iii. Glycerol mono-fatty acid esters;

iv. Fatty acid esters of polyethylene glycols of the formula:

$$R1-(O-CH_2-CH_2)_w-OH \text{ or}$$

$$R1-(O-CH_2-CH_2)_w-O-R1$$

wherein R1 is a stearoyl, lauroyl, oleoyl or palmitoyl residue; w ranges from 2–20;

v. Sorbitan fatty acid mono- and tri-esters of the formula:

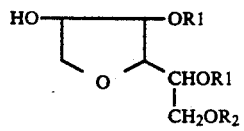

wherein: R1 is H or

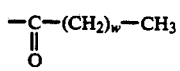

and
R2 is

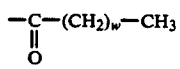

and w ranges from 10–16;

vi. Polyethoxylated sorbitan fatty acid esters of the formula:

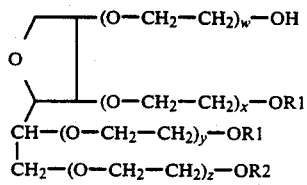

wherein: R1 is

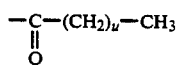

and
R2 is

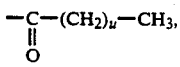

u ranges from 10–16 and (w+x+y+z) is 2–20.

4. A process according to claim 2 wherein the emulsion additionally comprises one or more structuring aids chosen from surfactants other than non-ionics in an amount of 0–50% and/or sterols in an amount of 0–100% by weight of the non-ionic emulsifier.

5. A process according to claim 2 wherein the perfume contains hydrophobic adjuncts in an amount of 0–30% by weight of the non-aqueous phase.

6. A process according to claim 2 wherein the aqueous phase contains hydrophilic adjuncts in an amount of 0–30% by weight of the aqueous phase.

7. The process according to claim 2 further comprising at least one of the following steps selected from the group consisting of: adding hydrophobic adjuncts to the non-aqueous phase and adding hydrophilic adjuncts to the aqueous phase, prior to mixing the aqueous phase and non-aqueous phase.

8. A process according to claim 6 wherein the emulsion comprises 4–25% by weight of non-ionic emulsifier(s), 10–50% of perfume and 25–86% of aqueous phase and the weight ratio of total emulsifier, including optional structuring aids, to perfume lies within the range 1:3 to 3:1 and the weight ratio of non-aqueous phase to aqueous phase lies within the range 1:2 to 4:3.

9. A process according to claim 1 wherein the emulsion is added to a detergent composition so as to produce a detergent product comprising 4–90% by weight of cationic, anionic, non-ionic or amphoteric surfactant, 0.15–98% of water, 0.01–30% of perfume and 0–60% by weight of optional adjuncts chosen from: abrasives, colours, dyes, preservatives, bleaches, optical brighteners, thickeners, emollients, conditioners, clarifiers, sunscreen agents, pearlescent agents, salts, therapeutic agents, structurants, stabilisers, and co-solvents.

10. A shampoo product produced from the process according to claim 9.

11. A solid or liquid soap produced from the process according to claim 9.

12. A foam bath product produced from the process according to claim 9.

13. A shower gel produced from the process according to claim 9.

14. A laundry washing product produced from the process according to claim 9.

15. A fabric conditioner produced from the process according to claim 9.

16. A domestic cleaner or bleach product produced from the process according to claim 9.

* * * * *